(12) United States Patent  
Hellstrom et al.

(10) Patent No.: US 7,847,943 B2
(45) Date of Patent: *Dec. 7, 2010

(54) WEB MEASUREMENT DEVICE

(75) Inventors: Ake Hellstrom, Columbus, OH (US); Rambod Naimi, Louth (IE); Michael O'Hora, Louth (IE)

(73) Assignee: ABB Ltd. (IE)

( * ) Notice: Subject to any disclaimer, the term of this patent is extended or adjusted under 35 U.S.C. 154(b) by 203 days.

This patent is subject to a terminal disclaimer.

(21) Appl. No.: 12/200,302

(22) Filed: Aug. 28, 2008

(65) Prior Publication Data
US 2009/0059232 A1 Mar. 5, 2009

Related U.S. Application Data

(60) Provisional application No. 60/969,373, filed on Aug. 31, 2007.

(51) Int. Cl.
*G01N 21/84* (2006.01)
(52) U.S. Cl. ............... 356/430; 356/600; 356/630; 250/559.27
(58) Field of Classification Search ......... 356/429–431, 356/600, 630–632, 237.1–237.5; 250/559.05, 250/559.06, 559.08, 559.09, 559.22, 559.24, 250/559.27
See application file for complete search history.

(56) References Cited

U.S. PATENT DOCUMENTS

| 4,449,398 | A | 5/1984 | Williams |
| 4,773,760 | A | 9/1988 | Makkonen |
| 5,479,720 | A | 1/1996 | Hellstrom |
| 6,281,679 | B1 | 8/2001 | King et al. |
| 6,313,915 | B1 * | 11/2001 | Yanagisawa et al. ........ 356/614 |
| 6,674,572 | B1 * | 1/2004 | Scheruebl et al. ........... 359/368 |
| 6,940,610 | B2 * | 9/2005 | Prinzhausen et al. ........ 356/609 |
| 7,599,068 | B2 * | 10/2009 | Lehmann .................... 356/489 |
| 2003/0024301 | A1 | 2/2003 | Jussi et al. |
| 2004/0109170 | A1 | 6/2004 | Schick |
| 2006/0109483 | A1 | 5/2006 | Marx et al. |
| 2006/0132808 | A1 | 6/2006 | Jasinski |
| 2006/0152231 | A1 | 7/2006 | Konermann et al. |
| 2007/0263203 | A1 | 11/2007 | Typpo |
| 2007/0263228 | A1 | 11/2007 | Typpo |

(Continued)

FOREIGN PATENT DOCUMENTS

DE 19733297 2/1992

(Continued)

OTHER PUBLICATIONS

Profilometer Roughness Tester Topography Dimensional Metrology, date unknown, http://www.microphotonics.com/micromeasureds.html.

(Continued)

*Primary Examiner*—Hoa Q Pham
(74) *Attorney, Agent, or Firm*—Michael C. Prewitt; Paul R. Katterle

(57) ABSTRACT

A sensor is provided that measures web caliper using optical and magnetic measuring devices. The optical measuring devices may employ a confocal chromatic aberration method to accurately determine the distance to the moving web and the magnetic devices may be ferrite core coil and target. Means of stabilizing a moving web are included for improving dynamic measurement accuracy.

19 Claims, 15 Drawing Sheets

U.S. PATENT DOCUMENTS

| | | | |
|---|---|---|---|
| 2008/0130013 A1 | 6/2008 | Stautmeister et al. | |
| 2008/0136091 A1 | 6/2008 | Shakespeare | |
| 2008/0158572 A1 | 7/2008 | Hughes | |
| 2008/0221837 A1* | 9/2008 | De Groot | 702/189 |
| 2009/0056156 A1* | 3/2009 | Hellstrom et al. | 33/501.02 |
| 2009/0059244 A1* | 3/2009 | Hellstrom et al. | 356/630 |

FOREIGN PATENT DOCUMENTS

| | | |
|---|---|---|
| DE | 20314026 | 1/2005 |
| DE | 102005002351 | 7/2006 |
| DE | 200510002351 | 7/2006 |
| EP | 1647799 | 4/2006 |
| EP | 1715290 | 10/2006 |
| JP | 4265814 | 9/1992 |
| JP | 2005099430 | 4/2005 |
| WO | 2002095475 | 11/2002 |
| WO | 2006119748 | 11/2006 |

OTHER PUBLICATIONS

Sensors Infrared Light White Light Chromatic Aberration Inverometric, date unknown, http://www.microphotonics.com/stilsensor.html.

Optical Measurement Systems, brochure, Fries Research & Technology, Apr. 2006.

LK-G Series Product Brochure, date unknown, http://www.keyence.com/products/vision/laser/lkg/lkg_features_1.php.

ISA, PCT/US2008/010064, Nov. 13, 2008.

* cited by examiner

WEB MEASUREMENT DEVICE

CROSS REFERENCE TO RELATED APPLICATION

This application claims the priority of U.S. provisional patent application Ser. No. 60/969,373 filed on Aug. 31, 2007 entitled "Web Thickness Measurement Device," the contents of which are relied upon and incorporated herein by reference in their entirety, and the benefit of priority under 35 U.S.C. 119(e) is hereby claimed

FIELD OF THE INVENTION

This invention relates to web measurement systems.

DESCRIPTION OF THE PRIOR ART

Sheet materials, such as paper, are produced in thin continuous webs and require highly accurate thickness (caliper) measurement and control. Commonly, these measurements are accomplished by means of sensors that physically contact the web at both the top and bottom side. Also, various non-contacting sensors have been developed that may be fully non-contacting (no physical contact), or sensors that contact physically contact sheet at only one side.

The speed of papermaking machinery has increased dramatically over time, while the web materials, for process economy, have become thinner and cheaper. This industry transition has illuminated the inherent limitations of contacting sensors, which may mark, scratch or otherwise damage the web. In particular, sensors that contact the sheet simultaneously from both sides have a risk of pinching sheets containing lumps or defects, resulting in the sensors causing holes or even sheet break on thin paper grades. Non-contacting sensors offer an advantage as they minimize the risks of such damage. Further, non-contacting sensors eliminate issues related to dirt buildup and wear that may cause measurement inaccuracies, thereby leading to frequent maintenance.

Existing non contacting thickness sensor solutions include single sided and dual sided air-bearings with magnetic distance measurement, single sided and dual sided laser triangulators with magnetic distance measurement, as well as other supplemental devices to improve sensor accuracy and stabilize the moving web.

One particular drawback to prior art non-contacting devices are the issues related to light penetration. Most paper has some degree of translucency, making the exterior surface position difficult to establish by traditional optical means. Cellulose fibers are relatively clear, and light reflected from the sheet does not radiate strictly from the sheet surface, but also from areas deeper in the paper. This often leads to optically measured thickness values that are too low. Therefore, using laser measurement may make a paper web appear thinner than the true thickness. These errors can be significant, and depending upon the paper grades, laser measurement can generate optical thickness measurements that are only 50% of the true value. Correct measurements are typically only accomplished if the measured sheet is coated or else has a very dense and opaque surface. Thus, none of the current non-contacting sensor solutions offer acceptable accuracy for the majority of paper grades, and furthermore, they tend to be complex in design and unreliable.

There is therefore a need in the art for a web measurement device that provides accurate measurements even when the traveling web is of a partially translucent type, such as paper.

SUMMARY OF THE INVENTION

In accordance with one aspect of the present invention, a sensor is provided for monitoring the attributes of a moving web. The sensor includes a sensor head positioned adjacent to a moving web. An optical sensor probe is positioned in the first sensor head, and includes an objective lens having an axial chromatism. A spectrograph is in communication with the objective lens to receive a reflected signal from the moving web. The spectrograph is adapted to measure the spectral width of the reflected signal and determine a web surface characteristic therefrom.

In accordance with another aspect of the present invention, a sensor is provided for monitoring a moving web. The sensor includes a first sensor head positioned on a first side of the moving web and a second sensor head positioned on a second side of the moving web, opposed to the first side. A first optical sensor probe is positioned in the first sensor head and includes a first objective lens having an axial chromatism. A second optical sensor probe is positioned in the second sensor head and includes a second objective lens having an axial chromatism. A spectrograph is in communication with the first and second objective lens to receive a reflected signal from the moving web. The spectrograph is adapted to measure the spectral width of the reflected signals and determine a surface characteristic of the first surface and the second surface.

In accordance with yet another aspect of the present invention, a method is provided for measuring a moving web. The method includes positioning an optical sensor probe adjacent to the moving web, the optical sensor probe having an objective lens having an axial chromatism; transmitting light through the objective lens toward the moving web; receiving a reflected signal through the objective lens; determining a spectral width of the reflected signal; determining a web surface characteristic based on the spectral width; and displaying the web surface characteristic.

DETAILED DESCRIPTION

Figure 1:
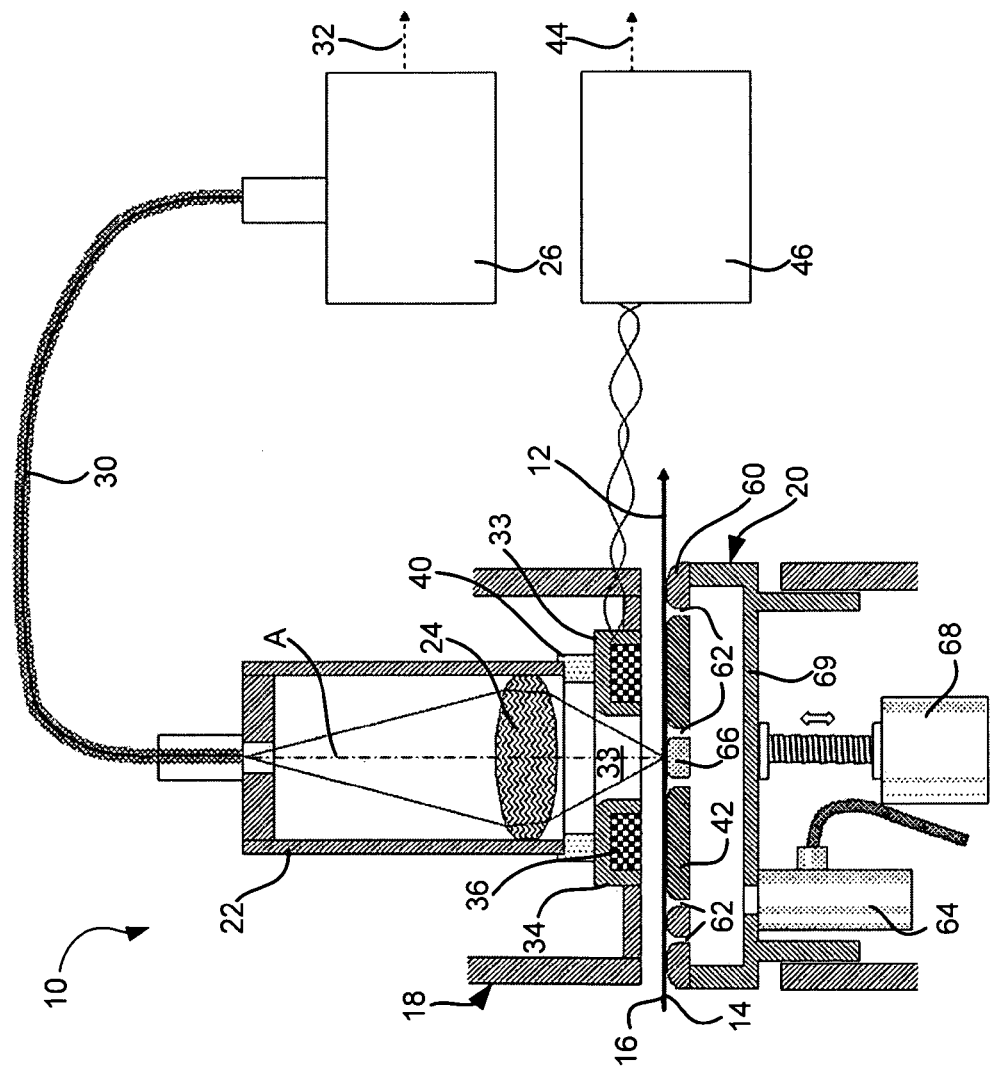
FIG. 1 shows a sectional and partially schematic view of a sensor according to the present invention.

Referring now to FIG. 1, a gauge measurement device (hereinafter device 10) is shown and generally indicated by the numeral 10. Device 10 may be installed and used in a web making process line, for example, a paper making line. When installed, device 10 is positioned in close proximity to a moving web 12 for measurement thereof. Though the present invention is particularly useful for paper making applications, device 10 may be used to measure any type of continuously produced web. Further, one or more devices 10 may be positioned at any point along the continuous web production process to continuously measure web thickness at multiple points in the process.

The web 12 may move at high speeds through device 10 in the machine direction D. In the example where web 12 is a paper product, production line speeds in paper manufacturing can reach 100 km per hour or more. Device 10 contacts a bottom surface 14 of web 12, while a top surface 16 is not contacted and is measured optically. A pair of opposed sensor heads cooperate to measure the thickness, or caliper, of web 12. A first sensor head 18 is positioned above top surface 16 and does not contact web 12. A second sensor head 20 contacts web 12 at bottom surface 14 and, as will become apparent, serves as a reference point for the measurement devices in first head 18.

First head 18 includes an optical displacement sensor probe 22 that employs a confocal chromatic aberration method to determine the distance from the probe to the top surface 16 of web 12. Probe 22 includes an objective lens 24 having axial chromatism, which results from the variation of the refractive index as a function of wavelength. Such a lens, if exposed to a point source of broad spectrum white light (such as from a fiber optic cable), will produce a continuum of monochromatic image points distributed along the optical axis A. When a surface of the measured sample, in the present case the web 12, intercepts the measurement axis A at point M, a singular monochromatic point image is focalized at M. Due to the confocal configuration, only the wavelength $\lambda_M$ will pass back to the spectrometer (through the fiber optic cable) with high efficiency because all other wavelengths are out of focus. If the web 12 is viewed through one or more transparent thin layers, each interface between adjacent layers reflects light at a different wavelength, and the spectrum of the detected light is composed of a series of spectral peaks. Such probes are configured and calibrated so that each spectral peak indicates a specific distance from the probe.

In the present embodiment, a light source and optical spectrograph 26 communicate with lens 24 through a fiber optic cable 30. White light travels through cable 30, is directed through objective lens 24 and onto the web 12. The reflected light that is focused back to the fiber optic cable 30 corresponds to the wavelength at that specific distance from lens 24. All other wavelengths will be out of focus. The spectrograph 26 produces a distance measurement 32 which represents the distance from probe 22 to the top surface 16 of web 12.

First sensor head 18 includes a second displacement measurement sensor in the form of an inductor 33 having a ferrite cup core 34 and a winding 36. Core 34 is annular and coaxial with lens 24, defining a center aperture 38 that provides an optical path between lens 24 and web 12. It is important to know the relative distances between inductor 33 and probe 22, thus ferrite cup core 34 is spaced from probe 22 by a spacer 40, the size of which is precisely known so that the exact distance to lens 24 is known. Inductor 33 magnetically measures the distance to a ferrite target plate 42 in second sensor head 20 which is in physical contact with bottom surface 14 of web 12. The inductance is converted to a displacement measurement 44 by electronic unit 46. Even though the ferrite based inductor system may advantageously provide a more accurate displacement measurement, prior art eddy current systems may also be utilized in the present invention. Further, it should be appreciated that first and second head 18 and 20 may be permanently fixed a predetermined distance apart. In such cases, magnetic measurement between heads 18 and 20 may be unnecessary.

Web thickness is thus determined by calculating the difference between the inductive sensor displacement measurement 44 (plus the height of spacer 40) and the optical sensor measurement 32.

Second sensor head 20 includes a contacting plate 60 within which resides ferrite target plate 42. Contacting plate 60 includes a plurality of suction slots 62 that are in communication with a vacuum chamber 63 positioned beneath contacting plate 60. A vacuum generator 64 draws air from vacuum chamber 63 which effectively draws air into chamber 63 through suction slots 62. In one embodiment vacuum generator 64 may be a venturi based vacuum generator operable with compressed air. Contacting plate 60 may also support an optical reference body 66 that is co-axial with lens 24.

Accurate measurements require calibration of the magnetic distance measurement 32, between inductor 33 and target plate 42, versus the optical distance measurement 44 between sensor probe 22 and optical reference body 66. A linear motion actuator 68 is included in second sensor head 20, and is utilized for calibration as well as vertical adjustment to attain the best operating distance/gap. Linear motion actuator 68 is capable of moving up or down a frame 69 that supports contacting plate 60, target plate 42 and reference body 66. As is known in the art, linear motion actuators such as lead screw equipped stepper motors or piezoelectric linear positioners are capable of reliably moving frame 69 a known distance with a high degree of accuracy.

Calibration can be performed when the web 12 is not present. The actuator 68 may move reference body 66, along with target plate 42, to a plurality of positions. The resulting responses from the optical and magnetic signals may then be compared. The magnetic gap measurement 44 may then be calibrated using the optical sensor 22 for a reference displacement measurement. In other words, the magnetic measurement may be forced to equal the optical measurement at each measurement point. This utilizes the pre-calibration of the optical sensor as a master measurement of the motion, and translates this motion of exactly the same amount to calibrate the magnetic sensor. The calibration can, for instance, involve a fine stepping linear motion of 3 mm total range while reading the optical and magnetic sensor signals every 0.01 mm of travel. In this way a continuous calibration curve can be periodically determined to correct for various issues such as drift, physical wear and misalignment.

Faulty thickness measurements will occur unless web 12 is in intimate contact with reference body 66. This is a challenge in many web production machines due to the very high travel speed of the web. For example, at high speeds, web 12 tends to experience aerodynamic and tension dynamic sheet vibrations, wrinkles and waves.

Figure 2:
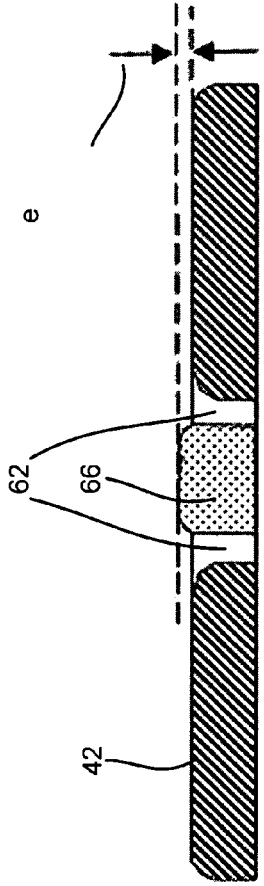
FIG. 2 shows a section view of the target plate and elevated optical reference body.
Figure 3:
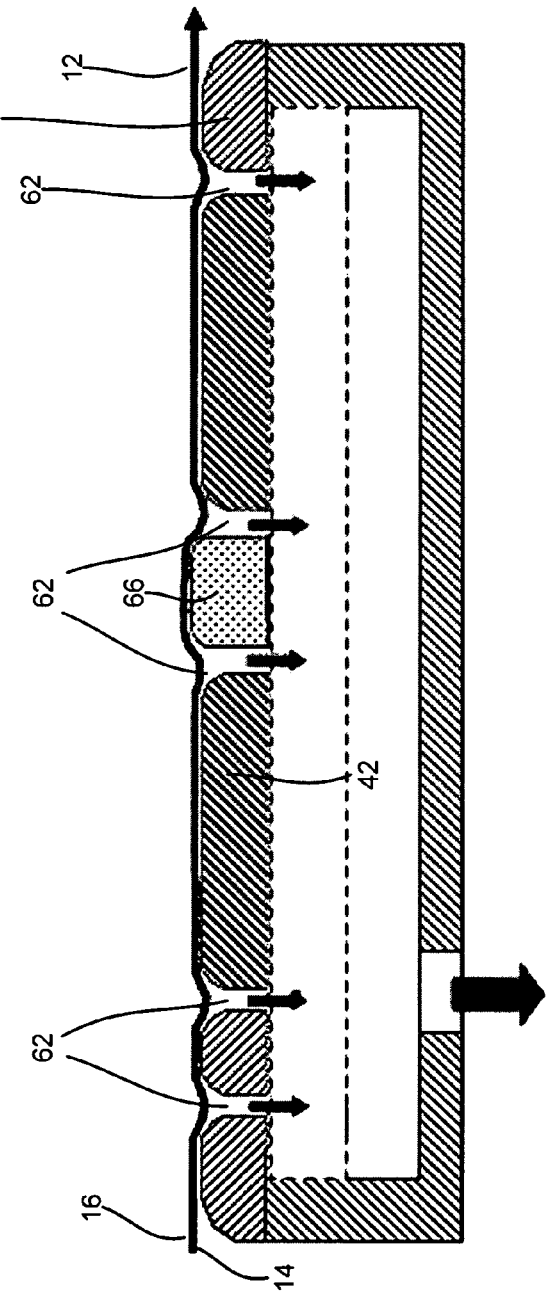
FIG. 3 shows a section view of the target plate and optical reference body.
Figure 4:
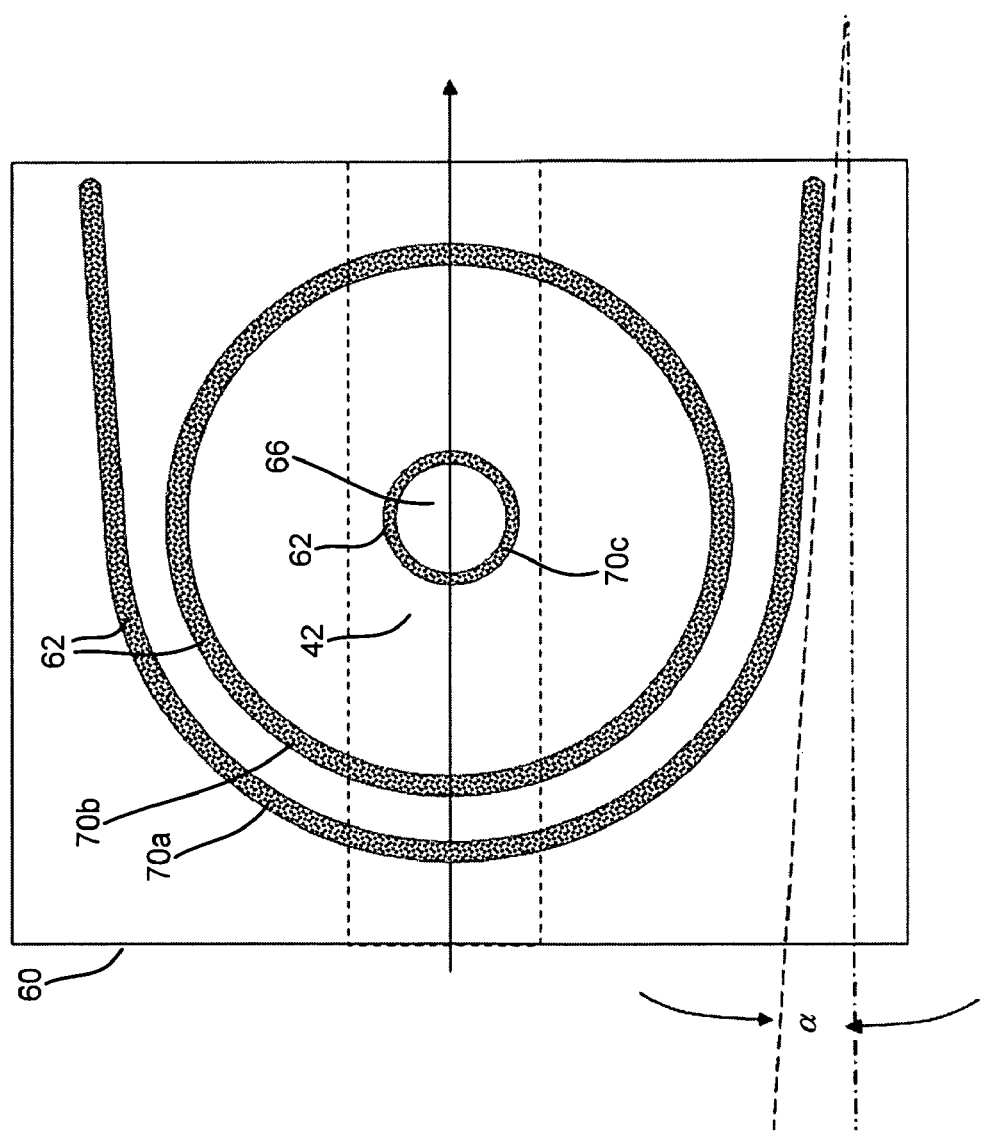
FIG. 4 shows top view of the contacting plate, target plate and optical reference body.

With reference to FIGS. 2-4, a more detailed view of contacting plate 60 is shown. As can be seen, in one embodiment, optical reference body 66 may be positioned a known distance e slightly above ferrite target plate 42. In one embodiment, optical reference body 66 extends above the top surface of target plate 42 by up to 0.5 mm. This arrangement enables more intimate contact of web 12 against optical reference body 66 at the point of optical measurement due to local stretching.

Further drawing the web 12 toward contacting plate 60 are the plurality of suction slots 62. The web 12 moving in direction D may advantageously be subjected to multiple suction slots 60 before passing over the reference body 66. The suction slots 60, in conjunction with the elevated reference body 66, combine to provide improved web contact with reference body 66. The web 12 has to slide over, for instance, three different suction zones 70a, 70b, and 70c, before reaching the reference body 66 where measurement takes place. This helps remove boundary layer air from disturbing the measurements, even at high speeds.

As can be seen in FIG. 4, web 12 moves in direction D across contact plate 60. The outermost suction slots 62 extend outwardly at an angle α from the machine direction D. In the present embodiment, the angle α is twenty five (25) degrees. In still other embodiments, particularly when used in very high speed machines the angle α may be from one (1) to five (5) degrees. This shallow angle acts to stretch the web 12 in the cross-machine direction to eliminate fluctuations and wrinkles. Further, the multiple suction zones 70a, 70b and 70c ensure that there is no loss of suction when measuring near the edge of web 12. It should be appreciated that other suction arrangements may be employed including, for example, concentric annular slots or other patterns such as plural holes.

The contacting plate 60, ferrite target plate 42 and optical reference body 66 are made of very smooth, low friction and wear resistant materials. The top surface of reference body 66 may be made from solid ceramic, sapphire, synthetic diamond or the like. Ferrite target plate 42 and contact plate 60 may include a smooth coating such as diamond film, plasma sprayed and lapped ceramics, or a thin ceramic sapphire cover that is post-machined and lapped. Ferrite target plate 60 and inductor 33 may also be mounted with exchanged locations between first sensor head 82 and second sensor head 84.

Figure 5:
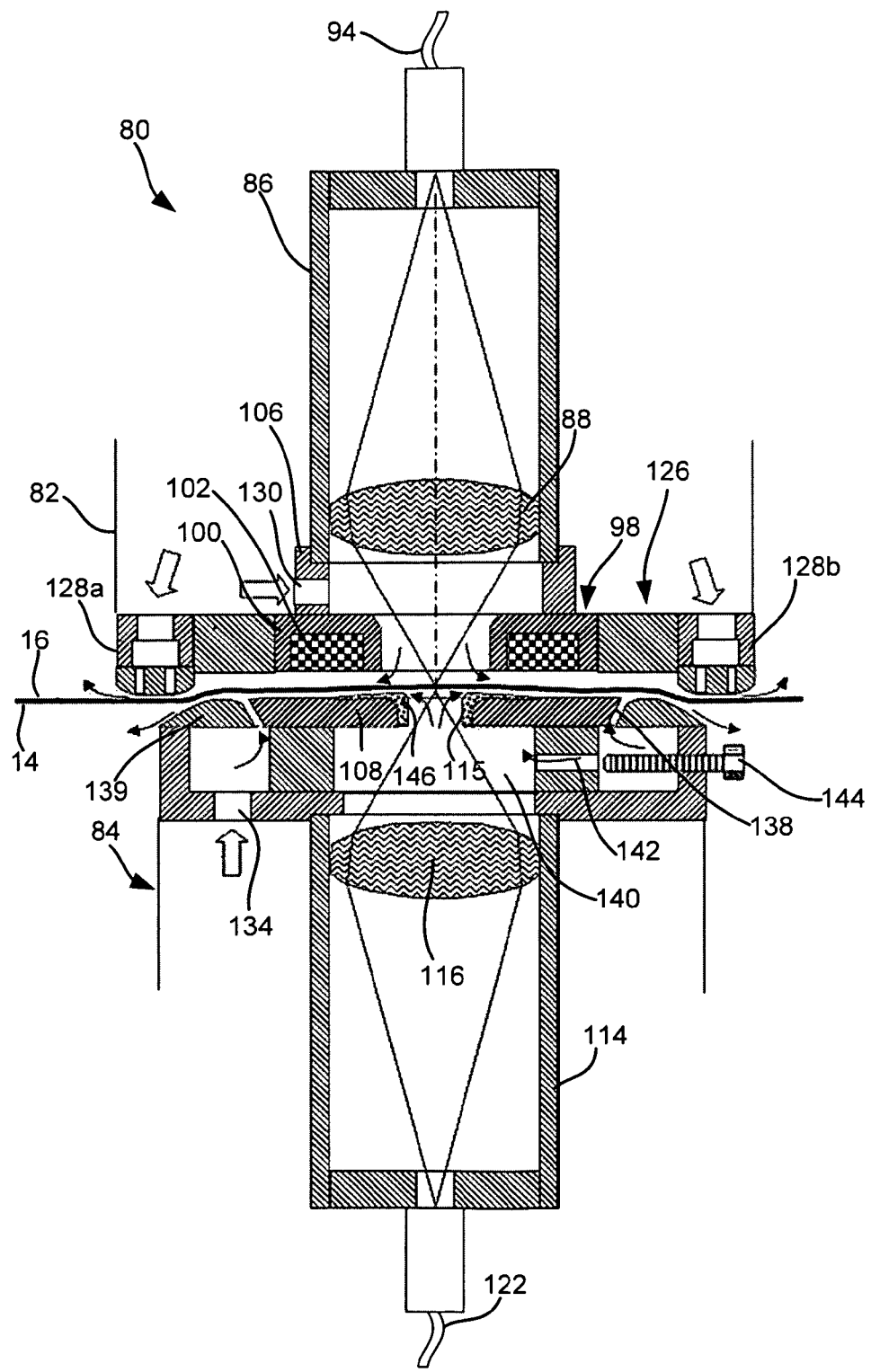
FIG. 5 shows a sectional view of a sensor according to an alternate embodiment of the present invention.
Figure 5A:
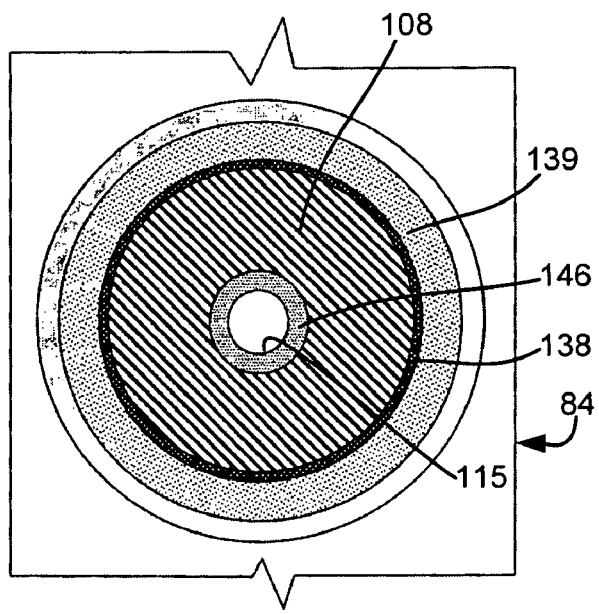
FIG. 5A shows an elevated view of the target plate of the embodiment of FIG. 5.
Figure 5B:
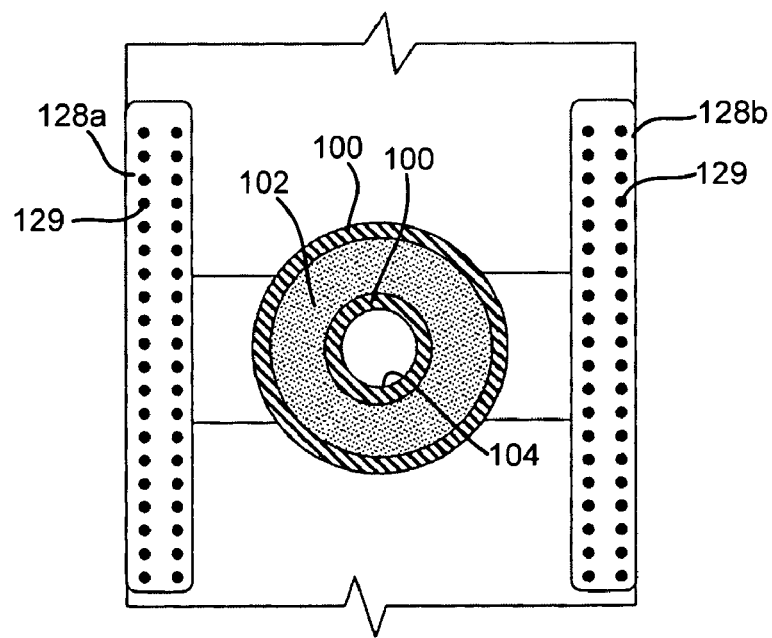
FIG. 5B shows an elevated view of the first sensor head having an air bearing arrangement.

Referring now to FIG. 5, an alternate embodiment of a sensor according to the present invention is shown and generally indicated by the numeral 80. Sensor 80 is adapted to measure web thickness without any direct contact with either side of web 12.

As with the previously described embodiment, sensor 80 may be positioned in close proximity to a moving web 12. The web thickness, or caliper, is measured by means of a first sensor head 82 that does not contact web 12 and an opposed second sensor head 84 that also does not contact web 12. It should be appreciated that, though the sensor heads are described as non-contacting, some incidental contact between web 12 and the sensor heads may occur. In the context of the present disclosure, non-contact means that the measurements themselves do not require physical contact between the web 12 and either of the sensor heads.

First head 82 includes an optical displacement sensor probe 86 that employs the confocal chromatic aberration method to determine the distance to the top surface 16 of web 12. Probe 86 includes an objective lens 88 which varies the refractive index as a function of wavelength. A light source and optical spectrograph (not shown) communicate with lens 88 through a fiber optic cable 94. Sensor probe 86 outputs a distance measurement which represents the distance from the lens 88 to top surface 16 of web 12.

First sensor head 82 further includes an inductor 98 having a ferrite cup core 100 with a winding 102. Core 100 is annular, defining a center aperture 104 that provides an optical path between lens 88 and web 12. It is important to know the relative distances between inductor 98 and probe 86, thus ferrite cup core 100 is spaced from probe 86 by a spacer 106, the size of which is precisely known so that the exact distance to lens 24 is known. Inductor 98 is coaxial with lens 88 and is utilized to magnetically measure distance to a ferrite target plate 108 in second sensor head 84. The inductance is converted to a displacement measurement by an electronic unit (not shown). As with the previous embodiment, inductor 98 and target plate 108 may be switched, with the target plate in first head 82 and the inductor positioned in he second head 84. Also, other magnetic measurement methods may be employed.

Second head 84 also includes an optical displacement sensor probe 114 that employs a confocal chromatic aberration method to determine the distance to the bottom surface 14 of web 12. Probe 114 includes an objective lens 116 which varies the refractive index as a function of wavelength. Probe 114 views the bottom surface 14 of web 12 through an aperture 115 in target plate 108. In order to minimize errors, the optical axis of second probe 114 is advantageously coaxial with the optical axis of first probe 86. In other words, the same point on the web 12 is measured at both the bottom surface 14 and top surface 16. A light source and optical spectrograph (not shown) communicate with lens 116 through a fiber optic cable 122. Sensor probe 114 produces a distance measurement which represents the distance from the lens 116 to the bottom surface 14 of web 12.

Thus, by measuring the distance between each sensor head 82 and 84 by inductor 98, and measuring the distance of each probe 86 and 114 to top 16 and bottom 14 of the web 12 by the confocal lenses 88 and 116, the thickness of web 12 may be measured.

Figure 5C:
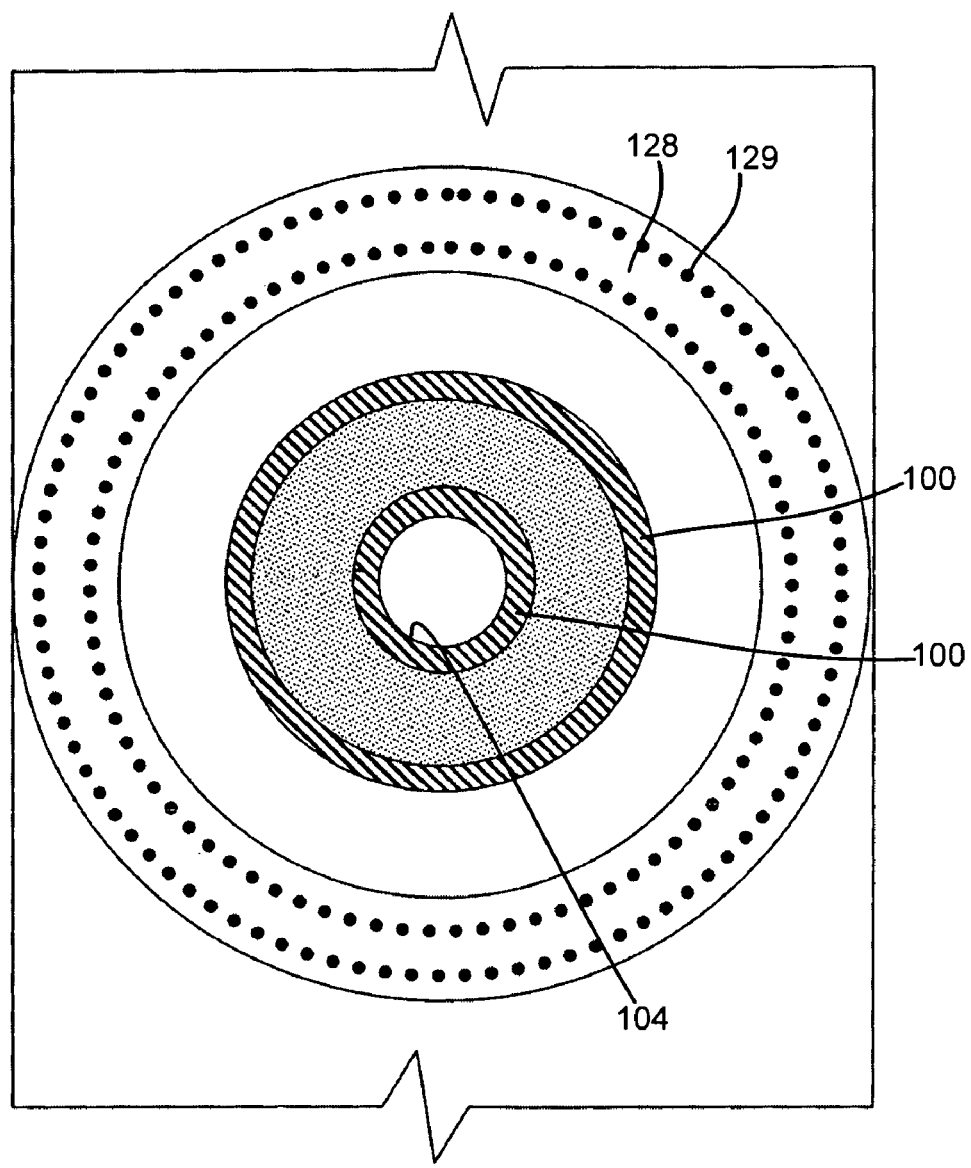
FIG. 5C shows an elevated view of the first sensor head having an alternate air bearing arrangement.

Sensor 80 includes an air-bearing arrangement 126 that acts to stabilize and flatten the moving web 12. Air-bearing arrangement 126 includes guide bars 128a and 128b that extend in the cross-machine direction and are positioned at opposed upstream and downstream ends of first sensor head 82. According to another embodiment, guide bar 128 may be circular, extending circumferentially around the entire sensor 80 (see FIG. 5C). In yet another embodiment, guide bars 128a and 128b may each be arced or curved. Guide bars 128 direct compressed air through a plurality of holes 129 downwardly toward web 12.

First head 82 also includes a port 130 that communicates with a chamber 132 located between lens 88 and web 12. Air is supplied through port 130, into chamber 132 and through aperture 104 toward web 12. As will be hereinafter discussed, this promotes the removal of wrinkles from web 12 at the area of measurement. Also, the evacuation of air through aperture 104 helps prevent contaminates from entering chamber 132 and dirtying lens 88.

Second sensor head 84 includes a port 134 that communicates compressed air to a peripheral chamber 136 that feeds a slot 138 at the periphery of ferrite target plate 108. Slot 138 may be annular and is positioned inwardly of guide bar 128 and may extend the entire periphery of the target plate 108. Slot 138 may be angled to direct air upwardly and outwardly. A ring 139 may be positioned outwardly of slot 138 that, in cross-section, curves away from web 12. In one embodiment, ring 138 includes an upwardly convex profile.

Chamber 136 communicates with a central chamber 140, located in front of lens 116, through a channel 142. The web 12 will, by this arrangement, float a small distance above ferrite target plate 108. The ratio of air flowing through aperture 115 and peripheral slot 134 may be controlled by a control valve 144. This ratio should be balanced to just barely lift web 12 away from contacting the central area of bottom head 84 while not deforming the local shape of web 12. Air flowing through the aperture 136 helps keep lens 88 clean and offers additional airbearing lift, to stretch web 12 without physically contact.

Air bearing arrangement 126 stretches web 12 to control flatness and parallelism for optical measurement. Guide bars may be adjusted to force web 12 to pass through sensor 80 in a zigzag or serpentine pattern in the gap between first sensor head 82 and second sensor head 83. This arrangement is effective in making the sheet flat by bending it in opposite directions as it passes through the sensor. The web stretching, at the optical point of measurement, is further promoted by an elevated lip 146, which is attached to target plate 108 surrounding aperture 115 and promotes a slight rise in the web at the area of the optical measurement. Lip 146 may be made of a smooth, non-magnetic and non-conductive material so that it does not interfere with magnetic measurements.

Figure 6:
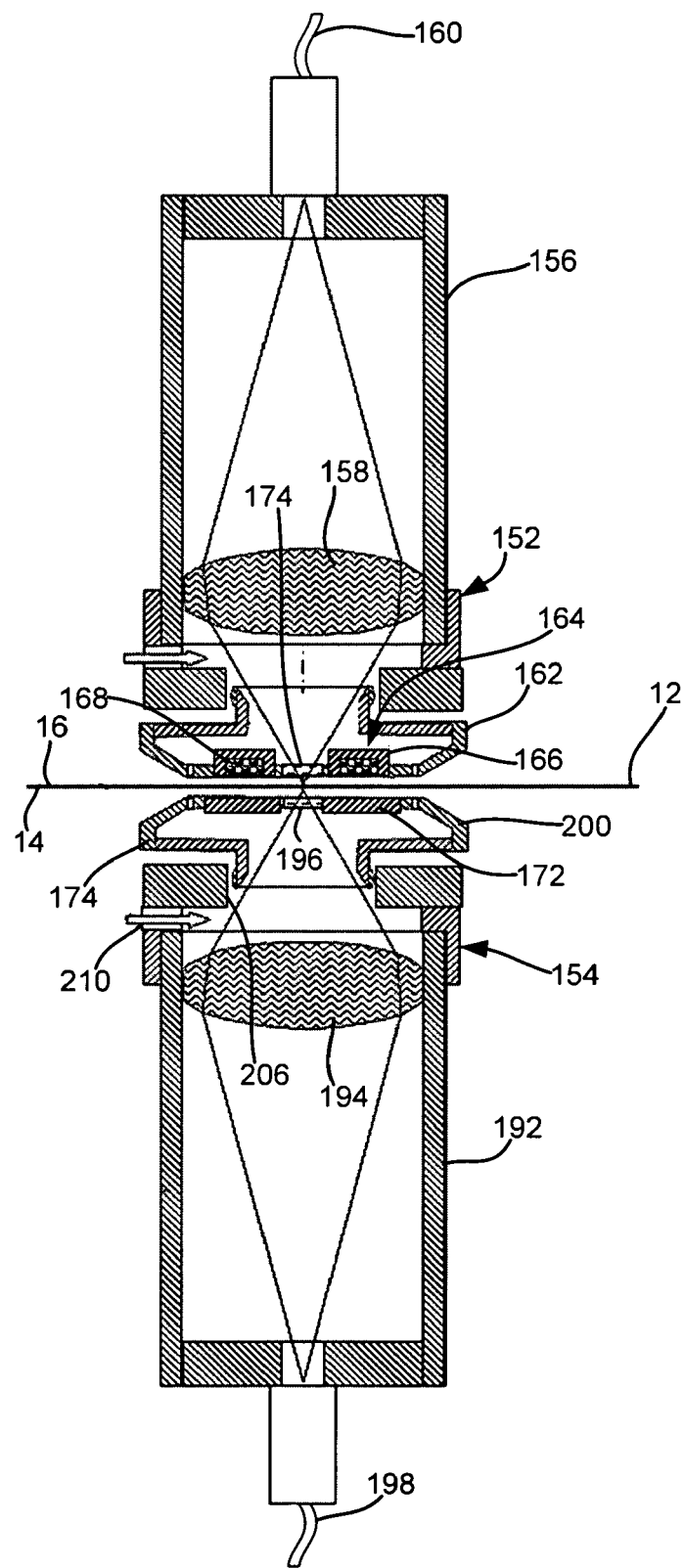
FIG. 6 shows a sectional view of a sensor according to a second alternate embodiment of the present invention.
Figure 7:
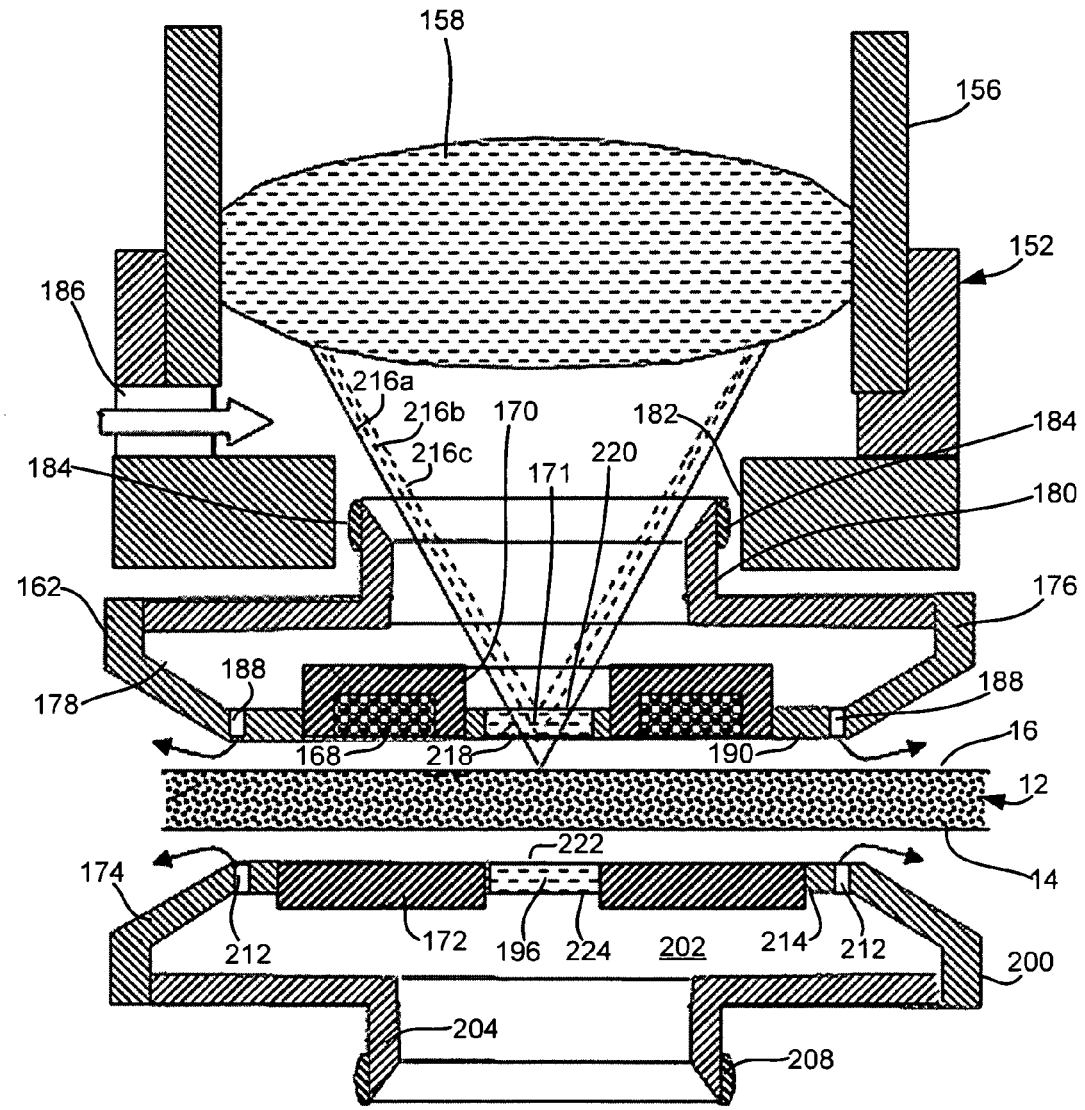
FIG. 7 shows an enlarged sectional view of the sensor of FIG. 6.

Referring now to FIGS. 6 and 7, a second alternate embodiment of a sensor is shown and generally indicated by the numeral 150. As with the embodiment described above, sensor 150 may be positioned in close proximity to a web 12 moving in direction D. The web thickness, or gauge, is measured by means of a first sensor head 152 that does not contact web 12 and a second sensor head 154 that also does not contact web 12.

First head 152 includes an optical displacement sensor probe 156 that employs a confocal chromatic aberration method to determine the distance to the top surface 16 of web 12. Probe 156 includes an objective lens 158 which varies the refractive index as a function of wavelength. A light source and optical spectrograph (not shown) communicate with lens 158 through a fiber optic cable 160. Sensor probe 156 measures the distance from the lens 158 to the top surface 16 of web 12.

First sensor head 152 further includes a first floating guide 162 that floats on a cushion of air above web 12. Floating guide 162 may be a body of rotational symmetry to assure symmetry and parallel lift of the air cushion. Guide 162 includes an inductor 164 having an annular ferrite cup core 166 with a winding 168. Core 166 defines a center aperture 170, within which is positioned a thin window 171. Window 171 may be a transparent or semitransparent material. In one or more embodiments window 171 is made of glass or sapphire. Inductor 164 is utilized to magnetically measure distance to a ferrite target plate 172 in a second floating guide 174. The inductance is converted to a displacement measurement by an electronic unit (not shown).

First floating guide 162 includes an outer body 176 that forms an interior chamber 178. A collar 180 extends upwardly from body 176 and is received in a bore 182. A spherical section 184 extends radially outwardly from collar 180 with a small clearance to bore 182, and by a small amount of escaping air forming a friction free airbearing around the spherical section 184 to allow free angular and axial articulation of guide 162 in the bore 182. The friction free suspension together with pneumatic force balance permits the guide 162 to achieve an equilibrium position parallel to, and at a relatively constant distance from the upper surface of web 12. Compressed air is received through a port 186 in first head 152. The air is thereafter communicated to chamber 178 through the inlet formed by collar 180. A plurality of spaced holes or circumferentially extending slots 188 are located on the bottom surface 190 of body 176 so that the compressed air is directed downwardly toward web 12. In this manner, first guide 162 is maintained above web 12 in a self-adjusting fashion.

Second head 154 includes an optical displacement sensor probe 192, axially aligned with probe 156, that employs a confocal chromatic aberration method to determine the distance to the bottom surface 14 of web 12. Probe 192 includes an objective lens 194 which varies the refractive index as a function of wavelength. Probe 192 views the bottom surface 14 of web 12 through a window 196 located centrally on target plate 172. Window 196 may be a transparent or semi-transparent material. In one or more embodiments window 196 is made of glass or sapphire. A light source and optical spectrograph (not shown) communicate with lens 194 through a fiber optic cable 198. Sensor probe 192 measures the distance from the lens 194 to the bottom surface 14 of web 12.

Second floating guide 174 includes an outer body 200 that forms an interior chamber 202. A spherical section 208 extends radially outwardly from collar 204 with a small clearance to bore 206, and by a small amount of escaping air forming a friction free airbearing around the spherical section 208 to allow free angular and axial articulation of guide 174 in the bore 206. The friction free suspension together with pneumatic force balance permits the guide 174 to achieve an equilibrium position parallel to, and at a relatively constant distance from the lower surface of web 12. Compressed air is received through a port 210 in second head 154. The air is thereafter communicated to chamber 202 through the inlet formed by collar 204. A plurality of spaced holes or slots 212 are located on the top surface 214 of body 200 so that the compressed air is directed from chamber 202 upwardly toward web 12. In this manner, second guide 174 is maintained below web 12 in a self-adjusting fashion.

The design parameters of guides 162 and 174, as well as air pressures, may be chosen so that each is maintained at about 100 μm away from the respective surface of web 12. Because guides 162 and 174 are maintained relatively close to web 12 (and consequently to each other) the inductor 164 and ferrite target plate 172 are likewise held in close proximity, and can therefore be designed to be highly accurate, as well as small in size.

Figure 8:
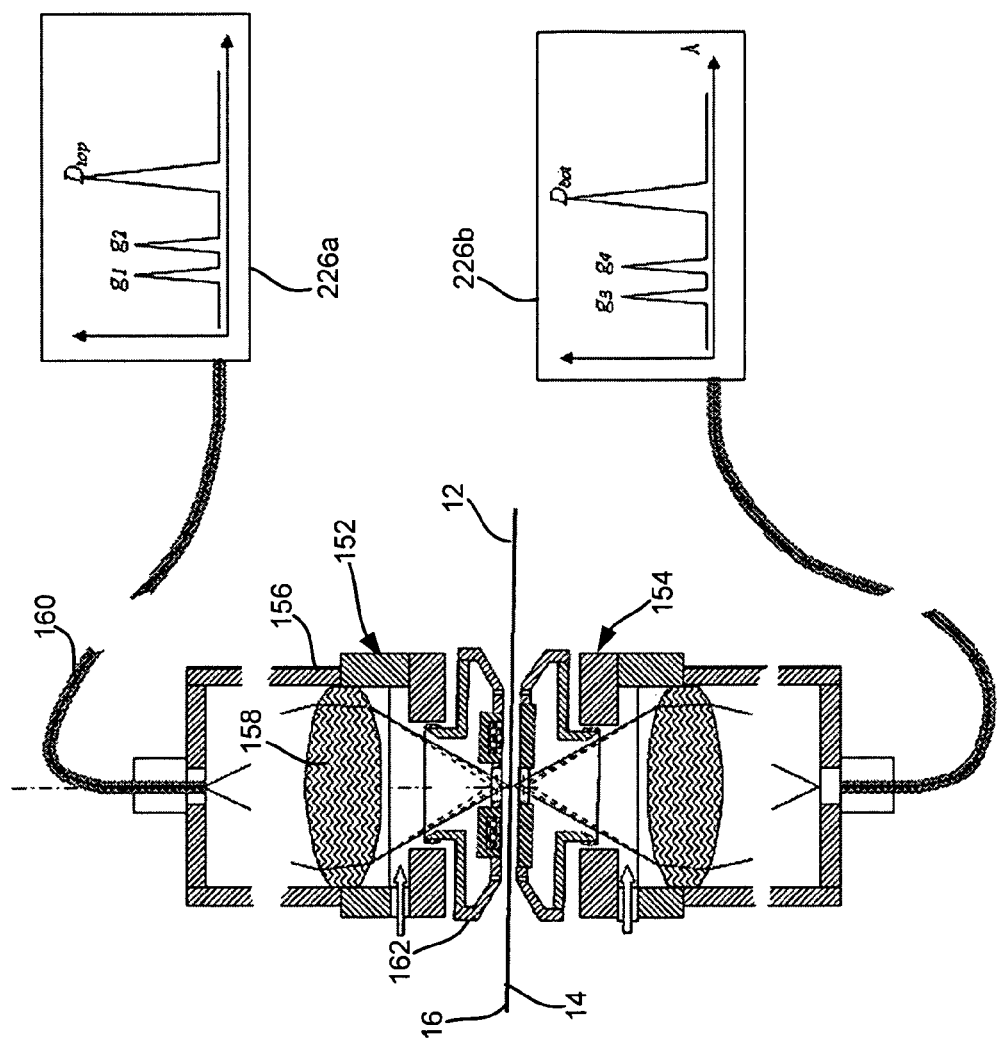
FIG. 8 shows a sectional and partially schematic view of the sensor of FIG. 6.

As discussed above, windows 171 and 196 may be glass, sapphire or the like and may be used to calibrate sensor 150. In one embodiment, windows 171 and 196 may be, for example 5 mm in diameter and precision machined to 0.2 mm thickness. As can be seen in FIG. 7 and 8, the chromatic aberration optical paths 216a, 216b and 216c that will return to the fiber optic cable in focus, originate from three different locations; 216a is reflected from top surface 16 of web 12, 216b is reflected from the bottom surface 218 of window 171 and 216c is reflected from the top surface 220 of window 171. Similarly, the chromatic paths of second probe 192 reflect from the bottom surface 14 of web 12, as well as the top and bottom surface 222 and 224 of window 196.

Probes 156 and 192 can distinguish multiple surface reflections simultaneously and determine each surface location separately. By this method, as guides 162 and 174 articulate, each of the three surfaces can be located and measured using the optical spectrograph. By also knowing the distance between each guide 162 and 174 using the inductor 164 and target plate 172, web thickness may be derived.

As noted above, when the optical path travels through windows 171 and 196, additional signals 216b and 216c are generated in the optical displacement measurement.

Referring now to FIG. 8, an exemplary chromatic separation of the peaks is shown in top and bottom spectrographs 226a and 226b respectively. The spectrograph 226a indicates three peaks for the three optical interfaces $g_1$, $g_2$ and $D_{top}$ for the top device and $g_3$, $g_4$ and $D_{bot}$ for the bottom device 226b. Because the window thickness can be precisely measured, and because the window thickness is very stable over time, these additional signals $g_1$, $g_2$, $g_3$, and $g_4$ can be used to dynamically correct for web tilt. Also, these signals can be used to determine the height of the guides 162 and 174 while measuring web 12.

Figure 9:
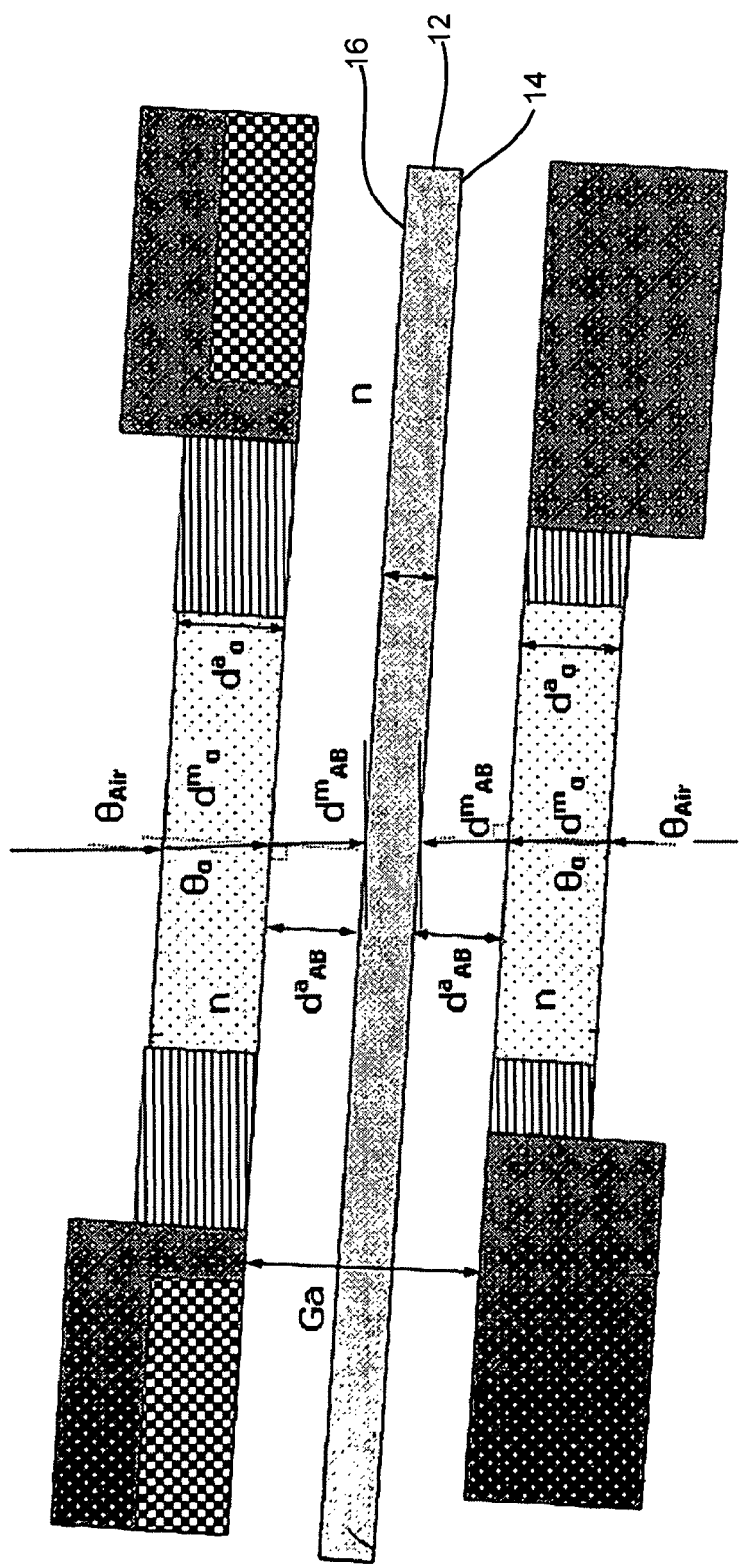
FIG. 9 shows an enlarged view of the floating guides proximate to the web.

The floating guides 162 and 174 are free to move with the moving web 12, and as a result may experience a varying degree of tilt during measurement. As a result, the optical axis and magnetic axis may no longer be parallel, which may cause measurement errors. With reference to FIG. 9, a method is shown to dynamically correct the resulting error when the optical axis is not normal to the moving web 12. The measured apparent thickness $t^m_{g1}$ and the actual thickness $t^a_{g1}$ of window 171 are used to dynamically determine the actual perpendicular distance $d^a_{AB1}$ between the guide 162 and the moving web 12. Because the actual thickness $t^a_{g1}$ of the glass window 171 is known (and constant), the measured distance between top and bottom glass surfaces 218 and 220 or 222 and 224 may be used to determine the tilt angle $\theta_{AB1}$ and $\theta_{AB2}$ of the respective floating guides 162 and 174. The actual guide height $d^a_{AB1}$ and $d^a_{AB2}$ is then calculated by the trigonometric steps below, using the measured guide heights $d^m_{AB1}$ and $d^m_{AB2}$.

$\theta_{g1} = \arccos(t^a_{g1}/t^m_{g1})$ $t^a_{g1}$ = actual glass thickness (Known)
$t^a_{g1}$ = measured glass thickness $\theta_{AB1} = \arcsin(n \sin(\theta_{g1}))$ n=refractive index, glass (Known)

$d^a_{AB1} = d^m_{AB1} \times \cos(\theta_{AB1})$ $\theta_{g2} = \arccos(t^a_{g2}/t^m_{g2})$ $t^a_{g2}$ = actual glass thickness (Known)
$t^a_{g2}$ = measured glass thickness $\theta_{AB2} = \arcsin(n \sin(\theta_{g2}))$ $d^a_{AB2} = d^m_{AB2} \times \cos(\theta_{AB2})$ Caliper=Gap $-(d^a_{AB1} + d^a_{AB2})$ Using this method, guides 162 and 174 can articulate to track local web tilt and flutter while still providing accurate measurements. It is also noted that the measured glass thickness will always be greater or equal to the actual thicknesses of the windows. It should be appreciated, however, that a suitable optical density correction may be required because a portion of the optical path is through a medium other than air.

Figure 10:
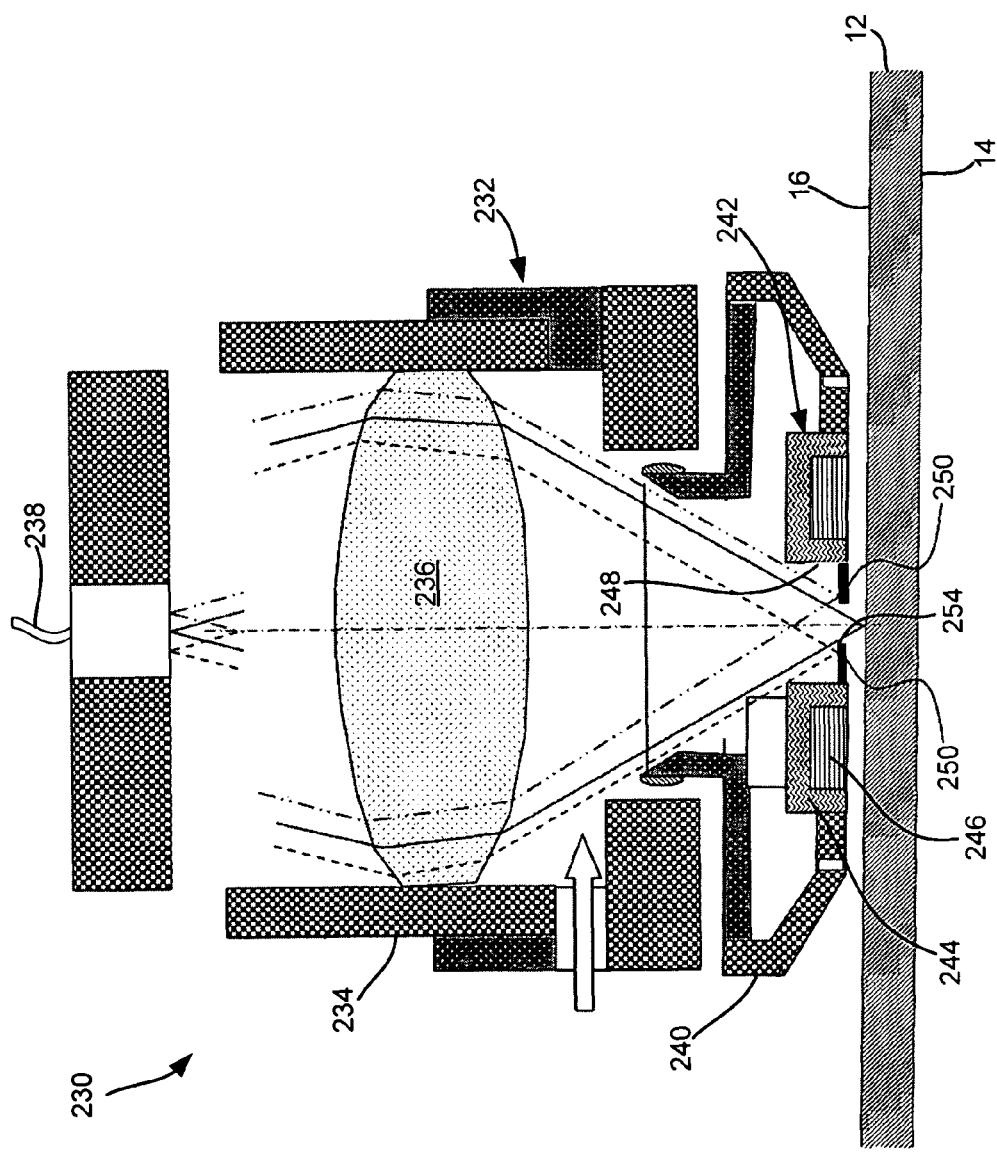
FIG. 10 shows a sectional view of a sensor according to a third alternate embodiment of the present invention.

Referring now to FIG. 10, a third alternate embodiment of a sensor is shown and generally indicated by the numeral 230. As with the embodiments described above, sensor 230 may be positioned in close proximity to a web 12. The web thickness, or gauge, is measured by means of a first sensor head 232 that does not contact web 12 and a second sensor head (not shown) that may generally mirror first head 232.

First head 232 includes an optical displacement sensor probe 234 that employs a confocal chromatic aberration method to determine the distance to the top surface 16 of web 12. Probe 234 includes an objective lens 236 which varies the refractive index as a function of wavelength. A light source and optical spectrograph (not shown) communicate with lens 236 through a fiber optic cable 238.

First sensor head 232 further includes a first guide 240 that floats on a cushion of air above web 12. Guide 240 includes an inductor 242 having an annular ferrite cup core 244 with a winding 246. Core 244 defines a center aperture 248, within which is positioned an annular plate 250. Inductor 242 is utilized to magnetically measure distance to a ferrite target plate (not shown) in the second guide (not shown) on the opposed side of web 12. The inductance is converted to a displacement measurement by an electronic unit (not shown).

Figure 11A:
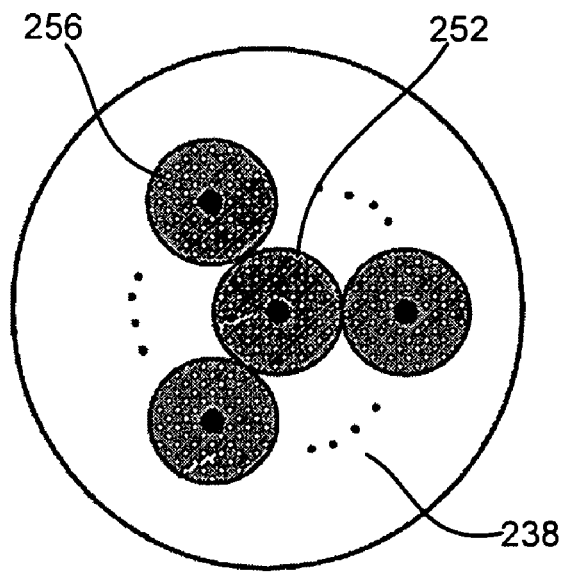
FIG. 11A shows a section view of one embodiment of a fiber optic cable according to the present invention.

Guide 240 is substantially similar to guide 162 with the exception that annular plate 250 is positioned within center aperture 248 instead of a window 171. This provides a non-obstructed view of the moving web surface 16 without a window that could potentially collect dirt and require regular cleaning. In this arrangement, probe 234 may include multiple fibers (of a fiber optic cable) optically viewing through the same lens 236. These fibers use the same lens 236 for delivery and collection of light, but have offset lateral positions. For example, in FIG. 11a an exemplary cross-sectional fiber arrangement is shown having a central fiber 252 that measures the distance to web 12 through the central aperture 254 of annular plate 250, while a plurality of fibers 256 are circumferentially spaced around central fiber 252 and measure distance to the annular reference plate 250. These measurements may be used to calculate the tilt of the guide 240. Because the tilt of guide 240 generally parallels the tilt of web 12, the measured guide tilt may be used to dynamically correct the measured gauge of web 12. It should be appreciated that the fiber arrangement of FIG. 11A, as well as FIGS. 11B and 11C may be used with on or more of the previous sensor embodiments.

Figure 11B:
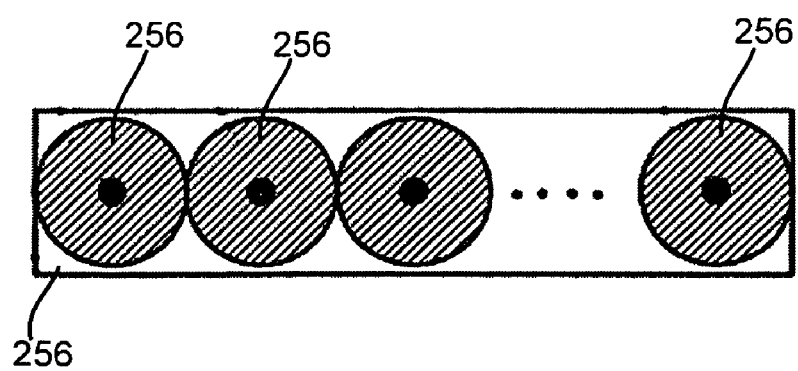
FIG. 11B shows a section view of a second embodiment of a fiber optic cable according to the present invention.
Figure 12:
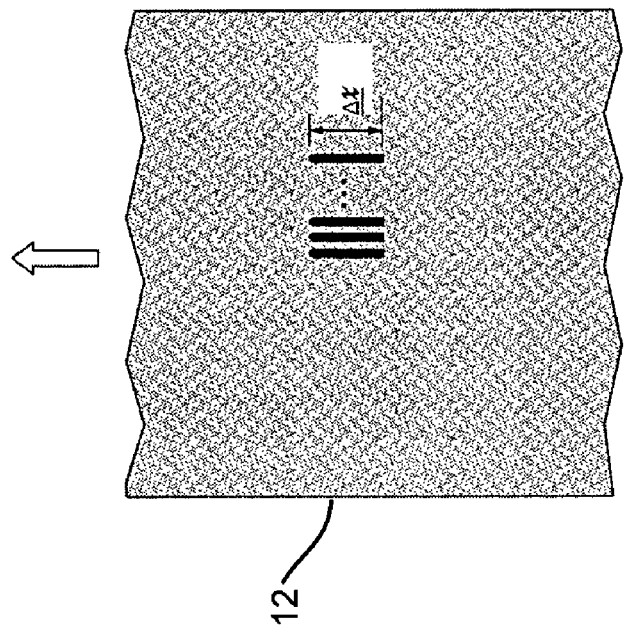
FIG. 12 shows a top view of the web and representations of the surface coverage using the fiber optic cable of FIG. 11B or 11C.
Figure 13:
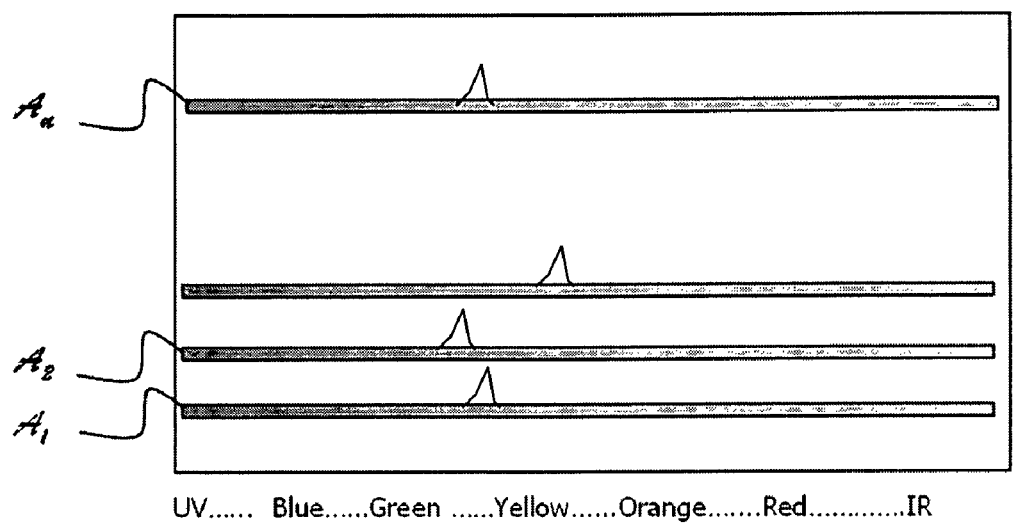
FIG. 13 shows a 2d imaging spectrograph.

Referring now to FIG. 11B, an alternate fiber arrangement is shown wherein a multitude of fibers 256 are arranged in a row in the cross-machine direction to be focused onto the material in the pattern shown in FIG. 12. Each individual fiber 256 may be interrogated by an imaging spectrograph. An exemplary resulting graph is shown in FIG. 13. As can be seen, each fiber is directed onto a different line across the 2D imaging spectrograph (A1 . . . An) and individual displacements are determined by signal processing. Each individual spectral line provides a high resolution surface profile. The fibers 256 can be arranged to be of comparable width to that of current online caliper measuring devices. Alternatively the average distance to the material surface can be estimated from the average spectral spread at each integration instance $\Delta x$. In yet another embodiment, the line of fibers 256 may be used to measure tilt along the axis of the machine direction, thus enabling automatic correction. In still another embodiment, measurements taken by fibers 256 may correlate to a roughness, porosity, or runnability measurement.

Figure 11C:
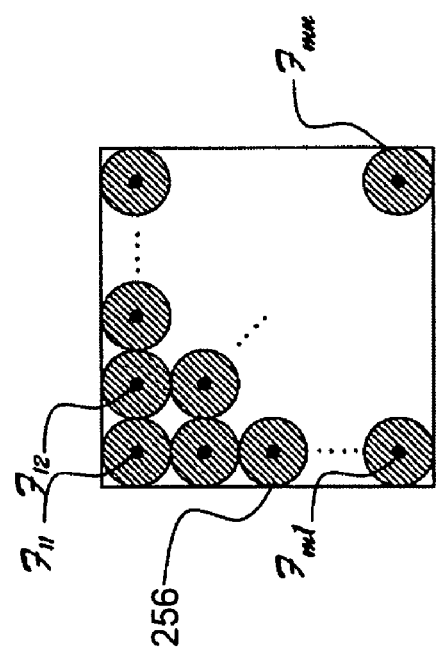
FIG. 11C shows a section view of a third embodiment of a fiber optic cable according to the present invention.

Referring now to FIG. 11C, an alternate fiber arrangement is shown, wherein the fibers 256 are arranged to obtain a two dimensional surface area profile. In this embodiment, multiple spectrographs may be separate or combined to make a 2d spectrograph (not shown) measures distance to the sheet at more than one point (i.e. pixels arranged in rows). This arrangement offers measurement of displacement as well as web tilt in both the cross-machine and machine direction. As previously discussed, web tilt can cause the thickness measurement to be in error due to the axial optical displacements combined with any non-concentricity of the two opposed optical probes. The measurement of web tilt permits compensation of measurement errors. The fibers 256 can be arranged to be of comparable width to that of current online caliper measuring devices. Alternatively, the average distance to the material surface may be produced by averaging the output of each fiber 256. In still another embodiment, provided surface intensity is high and integration time very small, measurements taken by fibers 256 may correlate to a 2D roughness, porosity, or runnability measurement.

Figure 14:
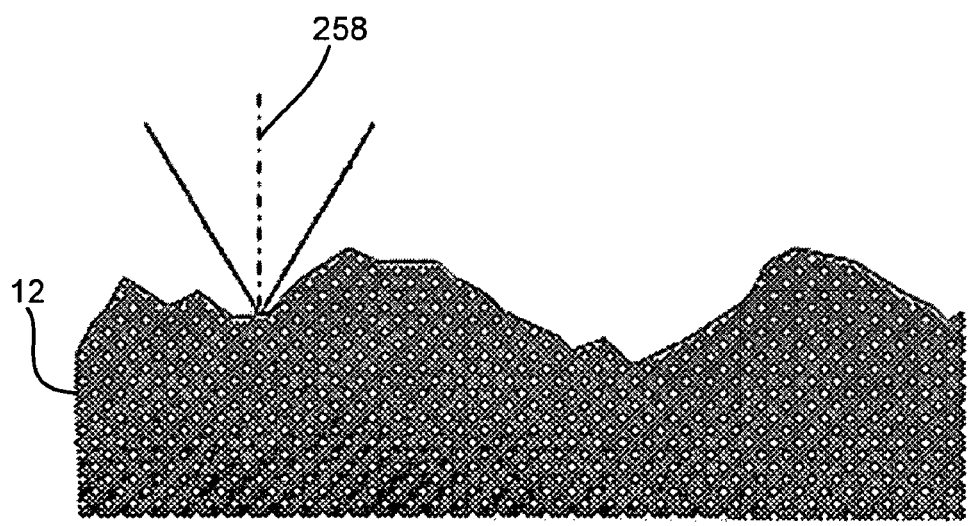
FIG. 14 shows a close-up side section view of the surface of a web.
Figure 15A:
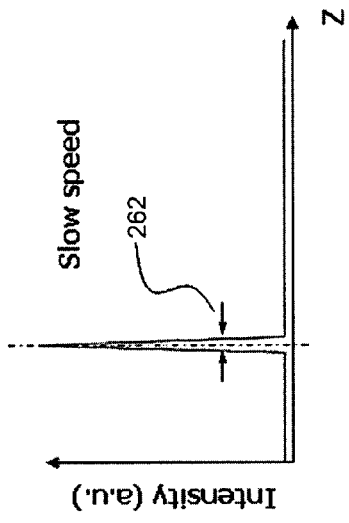
FIG. 15A shows a displacement graph representing the surface of a slow moving web.
Figure 15B:
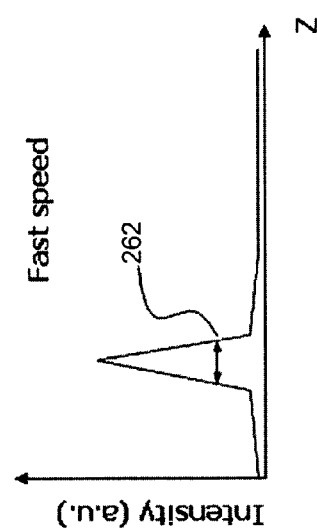
FIG. 15B shows a spectral graph representative of a point on the slow moving web.
Figure 16A:
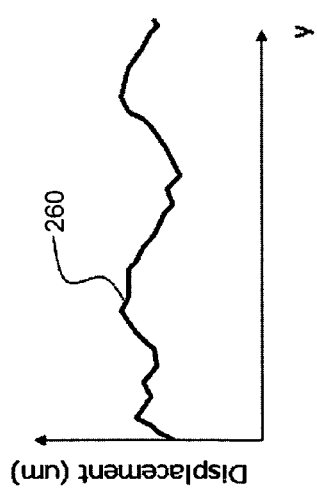
FIG. 16A shows a displacement graph representing the surface of a fast moving web.
Figure 16B:
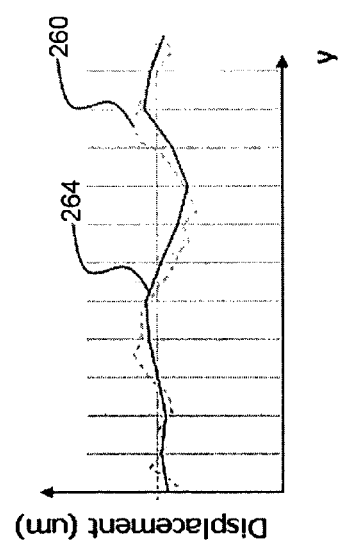
FIG. 16B shows a spectral graph representative of a point on the fast moving web.

Referring now to FIG. 14, a profile is shown of a web 12 with rough surface being probed by the optical beam 258. The resultant measured displacement 260 is shown in FIG. 15a which shows the expected spectra detected if the sample is moved at slow speed, or if integration time is very high, to resolve surface variations. The intensity at a given wavelength would be comparably very high in such an arrangement, as shown in FIG. 15b. If the same surface measurement is taken at a faster web speed or slower integration time, it can be seen in FIG. 16a that the measured distance is the averaged distance 264 measured by the probe during the spectrograph integration time. FIG. 16b shows the resultant spectral width 262 widening due to the rough surface integrated measurement. A relationship can be found analytically and/or empirically on the amount of spread as a function of integration distance and surface roughness. This offers multiple benefits, the surface topography can be used as an on-line sheet smoothness or gloss indicator, and the sheet thickness measurement may be corrected for topography induced measurement errors.

It is to be understood that the description of the foregoing exemplary embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A sensor for monitoring the attributes of a moving web, the sensor comprising:
   a sensor head positioned adjacent a moving web;
   an optical sensor probe, positioned in said first sensor head, and including an objective lens having an axial chromatism;
   a spectrograph in communication with the objective lens to receive a reflected signal from the moving web, said spectrograph being adapted to measure the spectral width of said reflected signal and determine a web surface characteristic therefrom.

2. The sensor of claim 1 wherein said characteristic is surface roughness.

3. The sensor of claim 1 wherein said characteristic is gloss.

4. The sensor of claim 1 wherein said characteristic is porosity.

5. The sensor of claim 1 wherein said characteristic is the thickness of transparent films deposited on the moving web.

6. The sensor of claim 1 wherein said characteristic is surface smoothness.

7. The sensor of claim 1 wherein the distance from said sensor head a first side of the moving web is determined by said spectrograph using confocal chromatic aberration.

8. The sensor of claim 7 further including:
   a second sensor head positioned on a second side of the moving web, opposed to said first side;
   an annular inductor positioned in said first or second sensor head and including a ferrite core and a winding;
   a contacting plate secured to said second sensor head, and adapted to contact the second side of the moving web; and
   a target plate secured to said first or said second sensor head opposed from said inductor, wherein said inductor is adapted to measure the distance to said target plate.

9. A sensor for monitoring a moving web, the sensor comprising:
   a first sensor head positioned on a first side of the moving web;
   a second sensor head positioned on a second side of the moving web, opposed to said first side;
   a first optical sensor probe positioned in said first sensor head including an first objective lens having an axial chromatism;
   a second optical sensor probe positioned in said second sensor head and including a second objective lens having an axial chromatism;
   a spectrograph in communication with said first and second objective lens to receive a reflected signal from the moving web, said spectrograph being adapted to measure the spectral width of said reflected signals and determine a surface characteristic of said first surface and said second surface.

10. The sensor of claim 9 wherein said characteristic is surface roughness.

11. The sensor of claim 9 wherein said characteristic is gloss.

12. The sensor of claim 9 wherein said characteristic is the thickness of transparent films deposited on the moving web.

13. The sensor of claim 9 wherein the distance from said sensor head a first side of the moving web is determined by said spectrograph using confocal chromatic aberration.

14. The sensor of claim 9 wherein said characteristic is surface smoothness.

15. A method of measuring a moving web, the method comprising:
   positioning an optical sensor probe adjacent to the moving web, said optical sensor probe having an objective lens having an axial chromatism;
   transmitting light through the objective lens toward the moving web;
   receiving a reflected signal through the objective lens;
   determining a spectral width of the reflected signal;
   determining a web surface characteristic based on the spectral width; and
   displaying the web surface characteristic.

16. The method of claim 15 wherein said characteristic is surface roughness.

17. The method of claim 15 wherein said characteristic is gloss.

18. The method of claim 15 wherein said characteristic is the thickness of transparent films deposited on the moving web.

19. The method of claim 15 wherein said characteristic is surface smoothness.

* * * * *